United States Patent
Eby

(10) Patent No.: US 11,284,592 B1
(45) Date of Patent: *Mar. 29, 2022

(54) SOYBEAN CULTIVAR 91030603

(71) Applicants: Monsanto Technology LLC, St. Louis, MO (US); Stine Seed Farm, Inc., Adel, IA (US)

(72) Inventor: William H. Eby, Panora, IA (US)

(73) Assignees: Monsanto Technology LLC, St. Louis, MO (US); Stine Seed Farm, Inc., Adel, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/018,573

(22) Filed: Sep. 11, 2020

(51) Int. Cl.
*A01H 6/54* (2018.01)
*A01H 5/10* (2018.01)

(52) U.S. Cl.
CPC ............... *A01H 6/542* (2018.05); *A01H 5/10* (2013.01)

(58) Field of Classification Search
CPC .................................................... A01H 6/542
See application file for complete search history.

(56) References Cited

U.S. PATENT DOCUMENTS

| | | | |
|---|---|---|---|
| 5,850,019 A | 12/1998 | Maiti et al. | |
| 6,051,753 A | 4/2000 | Comai et al. | |
| 6,660,911 B2 | 12/2003 | Fincher et al. | |
| 6,949,696 B2 | 9/2005 | Fincher et al. | |
| 7,141,722 B2 | 11/2006 | Fincher et al. | |
| 7,608,761 B2 | 10/2009 | Baley et al. | |
| 7,632,985 B2 | 12/2009 | Malven et al. | |
| 7,812,224 B2 | 10/2010 | Weeks et al. | |
| 7,838,729 B2 | 11/2010 | Feng et al. | |
| 7,855,326 B2 | 12/2010 | Feng et al. | |
| 7,884,262 B2 | 2/2011 | Clemente et al. | |
| 7,939,721 B2 | 5/2011 | Arnevik et al. | |
| 8,017,756 B2 | 9/2011 | De Beuckeleer | |
| 8,053,184 B2 | 11/2011 | Malven et al. | |
| 8,119,380 B2 | 2/2012 | Weeks et al. | |
| 8,207,092 B2 | 6/2012 | Bhatti et al. | |
| 8,501,407 B2 | 8/2013 | Brinker et al. | |
| 8,629,323 B2 | 1/2014 | Weeks et al. | |
| 8,700,336 B2 | 4/2014 | Van Den Bulcke et al. | |
| 8,754,011 B2 | 6/2014 | Bhatti et al. | |
| RE45,048 E | 7/2014 | Feng et al. | |
| 8,952,142 B2 | 2/2015 | De Beuckeleer | |
| 8,975,486 B1 | 3/2015 | Eby | |
| 9,017,947 B2 | 4/2015 | Malven et al. | |
| 9,062,324 B2 | 6/2015 | Mason et al. | |
| 9,447,428 B2 | 9/2016 | Brinker et al. | |
| 9,683,242 B2 | 6/2017 | Mason et al. | |
| 9,944,945 B2 | 4/2018 | Malven et al. | |
| 10,555,492 B1 * | 2/2020 | Eby | A01H 6/542 |
| 10,738,320 B2 | 8/2020 | Malven et al. | |

OTHER PUBLICATIONS

U.S. Appl. No. 17/018,586, filed Sep. 11, 2020, Eby.
U.S. Appl. No. 17/018,598, filed Sep. 11, 2020, Eby.
U.S. Appl. No. 17/018,603, filed Sep. 11, 2020, Eby.
Eshed et al., "Less-than-additive epistatic interactions of quantitative trait loci in tomato," *Genetics*, 143(4):1807-1817, 1996.
Kraft et al., "Linkage disequilibrium and fingerprinting in sugar beet," *Theor Appl Genet*, 101(3):323-326, 2000.
Willmot et al., "Genetic analysis of brown stem rot resistance in soybean," *Crop Sci*, 29(3):672-674, 1989.
Poehlman et al., "Methods in plant breeding," *Breeding Field Crops*, 4th ed., Iowa State Press, pp. 172-174, 1995.
Narvel et al., "A retrospective DNA marker assessment of the development of insect resistant soybean," *Crop Sci*, 41(6):1931-1939, 2001.
Goldman et al., "Molecular markers associated with maize kernel oil concentration in an Illinois High Protein x Illinois Low Protein cross," *Crop Sci*, 34(4):908-915, 1994.
Variety specific information as indicated in transmittal letter of Jan. 8, 2021 Information Disclosure Statement for U.S. Appl. No. 17/018,573.

* cited by examiner

*Primary Examiner* — Brent T Page
(74) *Attorney, Agent, or Firm* — Dentons US LLP

(57) ABSTRACT

A soybean cultivar designated 91030603 is disclosed. The invention relates to the seeds of soybean cultivar 91030603, to the plants of soybean cultivar 91030603, to the plant parts of soybean cultivar 91030603, and to methods for producing progeny of soybean cultivar 91030603. The invention also relates to methods for producing a soybean plant containing in its genetic material one or more transgenes and to the transgenic soybean plants and plant parts produced by those methods. The invention also relates to soybean cultivars or breeding cultivars, and plant parts derived from soybean cultivar 91030603. The invention also relates to methods for producing other soybean cultivars, lines, or plant parts derived from soybean cultivar 91030603, and to the soybean plants, varieties, and their parts derived from use of those methods. The invention further relates to hybrid soybean seeds, plants, and plant parts produced by crossing cultivar 91030603 with another soybean cultivar.

20 Claims, No Drawings

SOYBEAN CULTIVAR 91030603

BACKGROUND OF THE INVENTION

The present invention relates to a new and distinctive soybean cultivar, designated 91030603. All publications cited in this application are herein incorporated by reference.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possesses the traits to meet the program goals. The goal is to combine in a single cultivar an improved combination of desirable traits from the parental germplasm. These important traits may include, but are not limited to, higher seed yield, resistance to diseases and insects, better stems and roots, tolerance to drought and heat, altered fatty acid profile, abiotic stress tolerance, improvements in compositional traits, and better agronomic quality.

These processes, which lead to the final step of marketing and distribution, can take from six to twelve years from the time the first cross is made. Therefore, development of new cultivars is a time-consuming process that requires precise forward planning, efficient use of resources, and a minimum of changes in direction.

Soybean (*Glycine max*), is an important and valuable field crop. Thus, a continuing goal of soybean plant breeding is to develop stable, high yielding soybean cultivars that are agronomically sound. The reasons for this goal are to maximize the amount of grain produced on the land used and to supply food for both animals and humans. To accomplish this goal, the soybean breeder must select and develop soybean plants that have the traits that result in superior varieties.

The soybean is the world's leading source of vegetable oil and protein meal. The oil extracted from soybeans is used for cooking oil, margarine, and salad dressings. Soybean oil is composed of saturated, monounsaturated, and polyunsaturated fatty acids. It has a typical composition of 11% palmitic, 4% stearic, 25% oleic, 50% linoleic, and 9% linolenic fatty acid content ("Economic Implications of Modified Soybean Traits Summary Report," Iowa Soybean Promotion Board and American Soybean Association Special Report 92S (May 1990)). Changes in fatty acid composition for improved oxidative stability and nutrition are constantly sought after. Industrial uses of soybean oil, which is subjected to further processing, include ingredients for paints, plastics, fibers, detergents, cosmetics, lubricants, and biodiesel fuel. Soybean oil may be split, inter-esterified, sulfurized, epoxidized, polymerized, ethoxylated, or cleaved. Designing and producing soybean oil derivatives with improved functionality and improved oliochemistry is a rapidly growing field. The typical mixture of triglycerides is usually split and separated into pure fatty acids, which are then combined with petroleum-derived alcohols or acids, nitrogen, sulfonates, chlorine, or with fatty alcohols derived from fats and oils to produce the desired type of oil or fat.

Soybeans are also used as a food source for both animals and humans. Soybeans are widely used as a source of protein for poultry, swine, and cattle feed. During processing of whole soybeans, the fibrous hull is removed and the oil is extracted. The remaining soybean meal is a combination of carbohydrates and approximately 50% protein.

For human consumption, soybean meal is made into soybean flour, which is processed to protein concentrates used for meat extenders or specialty pet foods. Production of edible protein ingredients from soybean offers a healthy, less expensive replacement for animal protein in meats, as well as dairy type products.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary, not limiting in scope. In various embodiments, one or more of the above-described problems have been reduced or eliminated, while other embodiments are directed to other improvements.

According to the invention, there is provided a new soybean cultivar designated 91030603. This invention thus relates to the seeds of soybean cultivar 91030603, to the plants of soybean cultivar 91030603 and to methods for producing a soybean plant produced by crossing soybean cultivar 91030603 with itself or another soybean cultivar, and the creation of variants by mutagenesis or transformation of soybean cultivar 91030603.

This invention also relates to methods for introgressing a transgenic or mutant trait into soybean cultivar 91030603 and to the soybean plants and plant parts produced by those methods. This invention also relates to soybean cultivars or breeding cultivars and plant parts derived from soybean cultivar 91030603, to methods for producing other soybean cultivars or plant parts derived from soybean cultivar 91030603 and to the soybean plants, varieties, and their parts derived from the use of those methods. This invention further relates to soybean seeds, plants, and plant parts produced by crossing soybean cultivar 91030603 with another soybean cultivar. Thus, any such methods using the soybean cultivar 91030603 are part of this invention: selfing, backcrosses, hybrid production, crosses to populations, and the like. All plants produced using soybean cultivar 91030603 as at least one parent are within the scope of this invention. Advantageously, the soybean cultivar could be used in crosses with other, different, soybean plants to produce first generation ($F_1$) soybean hybrid seeds and plants with superior characteristics.

In another aspect, the present invention provides regenerable cells for use in tissue culture of soybean plant 91030603. The tissue culture will preferably be capable of regenerating plants having all the morphological and physiological characteristics of the foregoing soybean plant, and of regenerating plants having substantially the same genotype as the foregoing soybean plant. Preferably, the regenerable cells in such tissue cultures will be embryos, protoplasts, meristematic cells, callus, pollen, leaves, ovules, anthers, cotyledons, hypocotyl, pistils, roots, root tips, flowers, seeds, petiole, pods, or stems. Still further, the present invention provides soybean plants regenerated from the tissue cultures of the invention.

In addition to the exemplary aspects and embodiments described above, further aspects and embodiments will become apparent by study of the following descriptions.

DETAILED DESCRIPTION OF THE INVENTION

In the description and tables that follow, a number of terms are used. In order to provide a clear and consistent understanding of the specification and claims, including the scope to be given such terms, the following definitions are provided:

Abiotic stress: As used herein, abiotic stress relates to all non-living chemical and physical factors in the environment. Examples of abiotic stress include, but are not limited to, drought, flooding, salinity, temperature, and climate change.

Allele. Any of one or more alternative forms of a genetic sequence. In a diploid cell or organism, the two alleles of a given sequence typically occupy corresponding loci on a pair of homologous chromosomes.

Alter. The utilization of up-regulation, down-regulation, or gene silencing.

Backcrossing. A process in which a breeder crosses progeny back to one of the parental genotypes one or more times. Commonly used to introduce one or more locus conversions from one genetic background into another.

Breeding. The genetic manipulation of living organisms.

BU/A. Bushels per Acre. The seed yield in bushels/acre is the actual yield of the grain at harvest.

Brown Stem Rot. This is a visual disease score from 1 to 9 comparing all genotypes in a given test. The score is based on leaf symptoms of yellowing and necrosis caused by brown stem rot. Visual scores range from a score of 9, which indicates no symptoms, to a score of 1 which indicates severe symptoms of leaf yellowing and necrosis.

Cell. Cell as used herein includes a plant cell, whether isolated, in tissue culture, or incorporated in a plant or plant part.

Cotyledon. A cotyledon is a type of seed leaf. The cotyledon contains the food storage tissues of the seed.

Cross-pollination. Fertilization by the union of two gametes from different plants.

Diploid. A cell or organism having two sets of chromosomes.

Embryo. The embryo is the small plant contained within a mature seed.

Emergence. This score indicates the ability of the seed to emerge when planted 3" deep in sand at a controlled temperature of 25° C. The number of plants that emerge each day are counted. Based on this data, each genotype is given a 1 to 9 score based on its rate of emergence and percent of emergence. A score of 9 indicates an excellent rate and percent of emergence, an intermediate score of 5 indicates average ratings and a score of 1 indicates a very poor rate and percent of emergence.

$F_\#$. The "F" symbol denotes the filial generation, and the # is the generation number, such as $F_1$, $F_2$, $F_3$, etc.

Gene. As used herein, "gene" refers to a unit of inheritance corresponding to DNA or RNA that code for a type of protein or for an RNA chain that has a function in the organism.

Gene Silencing. The interruption or suppression of the expression of a gene at the level of transcription or translation.

Genotype. Refers to the genetic constitution of a cell or organism.

Haploid. A cell or organism having one set of the two sets of chromosomes in a diploid.

Hilum. This refers to the scar left on the seed that marks the place where the seed was attached to the pod prior to the seed being harvested.

Hypocotyl. A hypocotyl is the portion of an embryo or seedling between the cotyledons and the root. Therefore, it can be considered a transition zone between shoot and root.

Iron Deficiency Chlorosis. Iron deficiency chlorosis (IDC) is a yellowing of the leaves caused by a lack of iron in the soybean plant. Iron is essential in the formation of chlorophyll, which gives plants their green color. In high pH soils, iron becomes insoluble and cannot be absorbed by plant roots. Soybean cultivars differ in their genetic ability to utilize the available iron. A score of 9 means no stunting of the plants or yellowing of the leaves, and a score of 1 indicates the plants are dead or dying caused by iron deficiency, a score of 5 means plants have intermediate health with some leaf yellowing.

Linkage. Refers to a phenomenon wherein alleles on the same chromosome tend to segregate together more often than expected by chance if their transmission was independent.

Linkage Disequilibrium. Refers to a phenomenon wherein alleles tend to remain together in linkage groups when segregating from parents to offspring, with a greater frequency than expected from their individual frequencies.

Linoleic Acid Percent. Linoleic acid is one of the five most abundant fatty acids in soybean seeds. It is measured by gas chromatography and is reported as a percent of the total oil content.

Locus. A defined segment of DNA.

Lodging Resistance. Lodging is rated on a scale of 1 to 9. A score of 9 indicates erect plants. A score of 5 indicates plants are leaning at a 45° angle in relation to the ground and a score of 1 indicates plants are lying on the ground.

Maturity Date. Plants are considered mature when 95% of the pods have reached their mature color. The number of days are calculated either from August 31 or from the planting date.

Maturity Group. This refers to an agreed upon industry division of groups of soybean varieties based on zones in which they are adapted, primarily according to day length or latitude. They consist of very long day length varieties (Groups 000, 00, 0), and extend to very short day length varieties (Groups VII, VIII, IX, X).

Nucleic Acid. An acidic, chainlike biological macromolecule consisting of multiple repeat units of phosphoric acid, sugar and purine and pyrimidine bases.

Relative Maturity (RM). The term relative maturity is a numerical value that is assigned to a soybean cultivar based on comparisons with the maturity values of other varieties. The number preceding the decimal point in the RM refers to the maturity group. The number following the decimal point refers to the relative earliness or lateness within each maturity group. For example, a 3.0 is an early group III cultivar, while a 3.9 is a late group III cultivar.

Oil or Oil Percent. Soybean seeds contain a considerable amount of oil. Oil is measured by NIR spectrophotometry and is reported as a percentage basis.

Oleic Acid Percent. Oleic acid is one of the five most abundant fatty acids in soybean seeds. It is measured by gas chromatography and is reported as a percent of the total oil content.

Palmitic Acid Percent. Palmitic acid is one of the five most abundant fatty acids in soybean seeds. It is measured by gas chromatography and is reported as a percent of the total oil content.

Pedigree. Refers to the lineage or genealogical descent of a plant.

Pedigree Distance. Relationship among generations based on their ancestral links as evidenced in pedigrees. May be measured by the distance of the pedigree from a given starting point in the ancestry.

Percent Identity. Percent identity as used herein refers to the comparison of the homozygous alleles of two soybean varieties. Percent identity is determined by comparing a statistically significant number of the homozygous alleles of two developed varieties. For example, a percent identity of 90% between soybean cultivar 1 and soybean cultivar 2 means that the two cultivars have the same allele at 90% of their loci.

Percent Similarity. Percent similarity as used herein refers to the comparison of the homozygous alleles of a soybean cultivar such as soybean cultivar 91030603 with another plant, and if the homozygous allele of soybean cultivar 91030603 matches at least one of the alleles from the other plant, then they are scored as similar. Percent similarity is determined by comparing a statistically significant number of loci and recording the number of loci with similar alleles as a percentage. A percent similarity of 90% between soybean cultivar 91030603 and another plant means that soybean cultivar 91030603 matches at least one of the alleles of the other plant at 90% of the loci.

*Phytophthora* Tolerance. Tolerance to *Phytophthora* root rot is rated on a scale of 1 to 9, with a score of 9 being the best or highest tolerance ranging down to a score of 1 which indicates the plants have no tolerance to *Phytophthora*.

Phenotypic Score. The Phenotypic Score is a visual rating of general appearance of the cultivar. All visual traits are considered in the score including healthiness, standability, appearance, and freedom of disease. Ratings are scored from 1 being poor to 9 being excellent.

Plant. As used herein, the term "plant" includes reference to an immature or mature whole plant, including a plant from which seed, grain, or anthers have been removed. Seed or embryo that will produce the plant is also considered to be the plant.

Plant Height. Plant height is taken from the top of the soil to the top node of the plant and is measured in centimeters.

Plant Parts. As used herein, the term "plant parts" (or a soybean plant, or a part thereof) includes but is not limited to protoplasts, leaves, stems, roots, root tips, anthers, pistils, seed, grain, embryo, pollen, ovules, cotyledon, hypocotyl, pod, flower, shoot, tissue, petiole, cells, meristematic cells, and the like.

Pod. This refers to the fruit of a soybean plant. It consists of the hull or shell (pericarp) and the soybean seeds.

Progeny. As used herein, includes an $F_1$ soybean plant produced from the cross of two soybean plants where at least one plant includes soybean cultivar 91030603 and progeny further includes, but is not limited to, subsequent $F_2$, $F_3$, $F_4$, $F_5$, $F_6$, $F_7$, $F_8$, $F_9$, and $F_{10}$ generational crosses with the recurrent parental line.

Protein Percent. Soybean seeds contain a considerable amount of protein. Protein is generally measured by NIR spectrophotometry and is reported on an as is percentage basis.

Pubescence. This refers to a covering of very fine hairs closely arranged on the leaves, stems, and pods of the soybean plant.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Seed Protein Peroxidase Activity. Seed protein peroxidase activity refers to a chemical taxonomic technique to separate cultivars based on the presence or absence of the peroxidase enzyme in the seed coat. There are two types of soybean cultivars; those having high peroxidase activity (dark red color) and those having low peroxidase activity (no color).

Seed Yield (Bushels/Acre). The yield in bushels/acre is the actual yield of the grain at harvest.

Seeds Per Pound. Soybean seeds vary in seed size; therefore, the number of seeds required to make up one pound also varies. The number of seeds per pound affect the pounds of seed required to plant a given area and can also impact end uses.

Shattering. The amount of pod dehiscence prior to harvest. Pod dehiscence involves seeds falling from the pods to the soil. This is a visual score from 1 to 9 comparing all genotypes within a given test. A score of 9 means pods have not opened and no seeds have fallen out. A score of 5 indicates approximately 50% of the pods have opened, with seeds falling to the ground, and a score of 1 indicates 100% of the pods are opened.

Single Locus Converted (Conversion). Single locus converted (conversion), also known as coisogenic plants, refers to plants which are developed by a plant breeding technique called backcrossing and/or by genetic transformation to introduce a given locus that is transgenic in origin, wherein essentially all of the morphological and physiological characteristics of a soybean variety are recovered in addition to the characteristics of the locus transferred into the variety via the backcrossing technique or by genetic transformation.

Breeding History

The breeding history of the cultivar can be summarized as follows:

Populations containing soybean events GM_A19788, GM_A92205, A5547-127, with pedigree 11050339-52×(11050339-52×(11050339-52×GL4808A1-D1YN)) were created.

2017 F2 bulk populations were grown near Adel, Iowa and single plants were pulled.

2017-18 Plant rows were grown near Chacabuco, Argentina.

2018 Yield trials were grown at 6 locations in the Midwest.

2019 Based on yield from 2018 trials, 6013-06-03 was advanced to 2019 Elite yield trials.

6013-06-03 was given variety designation 91030603.

The cultivar has shown uniformity and stability, as described in the following variety description information. It has been self-pollinated a sufficient number of generations with careful attention to uniformity of plant type. The line has been increased with continued observation for uniformity. The results of an objective evaluation of the cultivar are presented in the table(s) that follow.

TABLE 1

| DESCRIPTION OF SOYBEAN CULTIVAR 91030603 | |
|---|---|
| Seed Coat Color (Mature Seed): | Yellow |
| Seed Coat Luster (Mature Seed): | Dull |
| Cotyledon Color (Mature Seed): | Yellow |
| Leaflet Shape: | Ovate |
| Growth Habit: | Indeterminate |
| Flower Color: | Purple |
| Hilum Color (Mature Seed): | Black |
| Plant Pubescence Color: | Light Tawny |
| Pod Wall Color: | Brown |
| Maturity Group: | IV |
| Relative Maturity: | 4.0 |
| Plant Lodging Score: | 6.9 |
| Plant Height (cm): | 99 |
| Seed Size (# seed/lb): | 2865 |
| Seed % Protein: | 36.7 |
| Seed % Oil: | 18.7 |

Physiological Responses: Contains GM_A19788 event conferring resistance to glyphosate herbicides including ROUNDUP. Event GM_A19788 is also known as event MON89788, which is the subject of U.S. Pat. No. 7,632,985, the disclosure of which is incorporated herein by reference. Event MON89788 is also covered by one or more of the following patents: U.S. Pat. Nos. 6,051,753; 6,660,911; 6,949,696; 7,141,722; 7,608,761; 8,053,184; 9,017,947; 9,944,945; and 10,738,320. Contains GM_A92205 event conferring resistance to dicamba herbicides. Event GM_A92205 is also known as event MON87708, which is the subject of U.S. Pat. No. 8,501,407, the disclosure of which is incorporated herein by reference. Event MON87708 is also covered by one or more of the following patents: U.S. Pat. Nos. 5,850,019; 7,812,224; 7,838,729; 7,884,262; 7,939,721; 8,119,380; 8,207,092; 8,629,323; 8,754,011; 9,447,428; and RE45,048. Contains event A5547-127, which confers tolerance to glufosinate herbicides. Event A5547-127, which also has the alternate designations "EE-GM2," "LL55," and "ACS-GM006-4," is the subject of U.S. Pat. Nos. 8,017,756, 8,700,336; 8,952,142; 9,062,324; and 9,683,242, the disclosures of which are incorporated herein by reference.

Disease Resistance: Soybean Cyst Nematode—rhg 1.

This invention is also directed to methods for producing a soybean plant by crossing a first parent soybean plant with a second parent soybean plant, wherein the first or second soybean plant is the soybean plant from cultivar 91030603. Further, both first and second parent soybean plants may be from cultivar 91030603. Therefore, any methods using soybean cultivar 91030603 are part of this invention: selfing, backcrosses, hybrid breeding, and crosses to populations. Any plants produced using soybean cultivar 91030603 as at least one parent are within the scope of this invention.

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformant plants obtained with the germplasm of the invention are intended to be within the scope of this invention.

Soybean cultivar 91030603 is believed to be similar to 11050339-52. While similar to 11050339-52 there are differences including at least that 91030603 has the GM_A92205 gene conferring resistance to dicamba herbicides, and the A5547-127 gene conferring resistance to glufosinate herbicides, while 91030603 does not contain these genes.

FURTHER EMBODIMENTS OF THE INVENTION

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, which are introduced into the genome using transformation or various breeding methods are referred to herein collectively as "transgenes." In some embodiments of the invention, a transgenic variant of soybean cultivar 91030603 may contain at least one transgene but could contain at least 1, 2, 3, 4, 5, 6, 7, 8, 9, 10, and/or no more than 15, 14, 13, 12, 11, 10, 9, 8, 7, 6, 5, 4, 3, or 2. Over the last 15 to 20 years several methods for producing transgenic plants have been developed, and the present invention also relates to transgenic variants of the claimed soybean cultivar 91030603.

Nucleic acids or polynucleotides refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least approximately 1000 nucleotides of sequence upstream from the 5' end of the coding region and at least approximately 200 nucleotides of sequence downstream from the 3' end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

One embodiment of the invention is a process for producing soybean cultivar 91030603 further comprising a desired trait, said process comprising introducing a transgene that confers a desired trait to a soybean plant of cultivar 91030603. Another embodiment is the product produced by this process. In one embodiment the desired trait may be one or more of herbicide resistance, insect resistance, disease resistance, decreased phytate, or modified fatty acid or carbohydrate metabolism. The specific gene may be any known in the art or listed herein, including: a polynucleotide conferring resistance to imidazolinone, dicamba, sulfonylurea, glyphosate, glufosinate, triazine, benzonitrile, cyclohexanedione, phenoxy propionic acid, and L-phosphinothricin; a polynucleotide encoding a *Bacillus thuringiensis* polypeptide; a polynucleotide encoding phytase, FAD-2, FAD-3, galactinol synthase, or a raffinose synthetic enzyme; or a polynucleotide conferring resistance to soybean cyst nematode, brown stem rot, *Phytophthora* root rot, soybean mosaic virus, or sudden death syndrome.

Numerous methods for plant transformation have been developed, including biological and physical plant transformation protocols. See, for example, Miki et al., "Procedures for Introducing Foreign DNA into Plants," in *Methods in Plant Molecular Biology and Biotechnology*, Glick and Thompson Eds., CRC Press, Inc., Boca Raton, pp. 67-88 (1993), and Armstrong, "The First Decade of Maize Transformation: A Review and Future Perspective," *Maydica*, 44:101-109 (1999). In addition, expression vectors and in vitro culture methods for plant cell or tissue transformation and regeneration of plants are available. See, for example, Gruber et al., "Vectors for Plant Transformation," in *Methods in Plant Molecular Biology and Biotechnology*, Glick and Thompson Eds., CRC Press, Inc., Boca Raton, pp. 89-119 (1993).

A genetic trait which has been engineered into the genome of a particular soybean plant may then be moved into the genome of another cultivar using traditional breeding techniques that are well known in the plant breeding arts. For example, a backcrossing approach is commonly used to move a transgene from a transformed soybean cultivar into an already developed soybean cultivar, and the resulting backcross conversion plant would then comprise the transgene(s).

Various genetic elements can be introduced into the plant genome using transformation. These elements include, but are not limited to, genes, coding sequences, inducible, constitutive and tissue specific promoters, enhancing sequences, and signal and targeting sequences. For example, see the traits, genes, and transformation methods listed in U.S. Pat. No. 6,118,055.

Included among various plant transformation techniques are methods that permit the site-specific modification of a plant genome, including coding sequences, regulatory elements, non-coding and other DNA sequences in a plant genome. Such methods are well-known in the art and include, for example, use of the CRISPR-Cas system, zinc-finger nucleases (ZFNs), and transcription activator-like effector nucleases (TALENs), among others.

Plant transformation may involve the construction of an expression vector which will function in plant cells. Such a vector can comprise DNA comprising a gene under control of, or operatively linked to, a regulatory element (for example, a promoter). The expression vector may contain one or more such operably linked gene/regulatory element combinations. The vector(s) may be in the form of a plasmid and can be used alone or in combination with other plasmids to provide transformed soybean plants using transformation methods as described below to incorporate transgenes into the genetic material of the soybean plant(s).

Expression Vectors for Soybean Transformation: Marker Genes

Expression vectors include at least one genetic marker operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Fraley et al., *Proc. Natl. Acad. Sci. USA,* 80:4803 (1983). Another commonly used selectable marker gene is the hygromycin phosphotransferase gene which confers resistance to the antibiotic hygromycin. Vanden Elzen et al., *Plant Mol. Biol.,* 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant (Hayford et al., *Plant Physiol.,* 86:1216 (1988); Jones et al., *Mol. Gen. Genet.,* 210:86 (1987); Svab et al., *Plant Mol. Biol.,* 14:197 (1990); Hille et al., *Plant Mol. Biol.,* 7:171 (1986)). Other selectable marker genes confer resistance to herbicides such as glyphosate, glufosinate, or bromoxynil (Comai et al., *Nature,* 317:741-744 (1985); Gordon-Kamm et al., *Plant Cell,* 2:603-618 (1990); Stalke et al., *Science,* 242:419-423 (1988)).

Selectable marker genes for plant transformation not of bacterial origin include, for example, mouse dihydrofolate reductase, plant 5-enolpyruvylshikimate-3-phosphate synthase, and plant acetolactate synthase (Eichholtz et al., *Somatic Cell Mol. Genet.,* 13:67 (1987); Shah et al., *Science,* 233:478 (1986); Charest et al., *Plant Cell Rep.,* 8:643 (1990)).

Another class of marker genes for plant transformation requires screening of presumptively transformed plant cells, rather than direct genetic selection of transformed cells, for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase, and chloramphenicol acetyltransferase (Jefferson, R. A., *Plant Mol. Biol. Rep.,* 5:387 (1987); Teeri et al., *EMBO J.,* 8:343 (1989); Koncz et al., *Proc. Natl. Acad. Sci. USA,* 84:131 (1987); DeBlock et al., *EMBO J.,* 3:1681 (1984)).

In vivo methods for visualizing GUS activity that do not require destruction of plant tissue are available (Molecular Probes, Publication 2908, IMAGENE GREEN, pp. 1-4 (1993); Naleway et al., *J. Cell Biol.,* 115:151a (1991)). However, these in vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells (Chalfie et al., *Science,* 263:802 (1994)). GFP and mutants of GFP may be used as screenable markers.

Expression Vectors for Soybean Transformation: Promoters

Genes included in expression vectors must be driven by a nucleotide sequence comprising a regulatory element (for example, a promoter). Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in a certain tissue are referred to as "tissue-specific." A "cell-type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell-type specific, and inducible promoters constitute the class of "non-constitutive" promoters. A "constitutive" promoter is a promoter that is active under most environmental conditions.

A. Inducible Promoters—An inducible promoter is operably linked to a gene for expression in soybean. Optionally, the inducible promoter is operably linked to a nucleotide sequence encoding a signal sequence which is operably linked to a gene for expression in soybean. With an inducible promoter the rate of transcription increases in response to an inducing agent.

Any inducible promoter can be used in the instant invention. See, Ward et al., *Plant Mol. Biol.,* 22:361-366 (1993). Exemplary inducible promoters include, but are not limited to, that from the ACEI system which responds to copper (Mett et al., *Proc. Natl. Acad. Sci. USA,* 90:4567-4571 (1993)); In2 gene from maize which responds to benzenesulfonamide herbicide safeners (Hershey et al., *Mol. Gen Genetics,* 227:229-237 (1991); Gatz et al., *Mol. Gen. Genetics,* 243:32-38 (1994)); or Tet repressor from Tn10 (Gatz et al., *Mol. Gen. Genetics,* 227:229-237 (1991)). A particularly preferred inducible promoter is a promoter that responds to an inducing agent to which plants do not normally respond. An exemplary inducible promoter is the inducible promoter from a steroid hormone gene, glucocorticoid response elements, the transcriptional activity of which is induced by a glucocorticoid hormone (Schena et al., *Proc. Natl. Acad. Sci. USA,* 88:10421-10425 (1991)).

B. Constitutive Promoters—A constitutive promoter is operably linked to a gene for expression in soybean or the constitutive promoter is operably linked to a nucleotide sequence encoding a signal sequence which is operably linked to a gene for expression in soybean.

Many different constitutive promoters can be utilized in the instant invention. Exemplary constitutive promoters include, but are not limited to, the promoters from plant viruses such as the 35S promoter from CaMV (Odell et al., *Nature,* 313:810-812 (1985)) and the promoters from such genes as rice actin (McElroy et al., *Plant Cell,* 2: 163-171 (1990)); ubiquitin (Christensen et al., *Plant Mol. Biol.,* 12:619-632 (1989); Christensen et al., *Plant Mol. Biol.,* 18:675-689 (1992)); pEMU (Last et al., *Theor. Appl. Genet.,* 81:581-588 (1991)); MAS (Velten et al., *EMBO J.,* 3:2723-2730 (1984)); and maize H3 histone (Lepetit et al., *Mol. Gen. Genetics,* 231:276-285 (1992); Atanassova et al., *Plant Journal,* 2 (3): 291-300 (1992)). The ALS promoter, an Xba1/Nco1 fragment 5' to the *Brassica napus* ALS3 structural gene (or a nucleotide sequence similarity to said Xba1/Nco1 fragment), represents a particularly useful constitutive promoter. See PCT Application WO 96/30530.

C. Tissue-Specific or Tissue-Preferred Promoters—A tissue-specific promoter is operably linked to a gene for expression in soybean. Optionally, the tissue-specific promoter is operably linked to a nucleotide sequence encoding a signal sequence which is operably linked to a gene for expression in soybean. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter such as that from the phaseolin gene (Murai et al., *Science,* 23:476-482 (1983); Sengupta-Gopalan et al., *Proc. Natl. Acad. Sci. USA,* 82:3320-3324 (1985)); a leaf-specific and light-induced promoter such as that from cab or rubisco (Simpson et al., *EMBO J.,* 4(11): 2723-2729 (1985); Timko et al., *Nature,* 318:579-582 (1985)); an anther-specific promoter such as that from LAT52 (Twell et al., *Mol. Gen. Genetics,* 217:240-245 (1989)); a pollen-specific promoter such as that from Zm13 (Guerrero et al., *Mol. Gen. Genetics,* 244:161-168 (1993)); or a microspore-preferred promoter such as that from apg (Twell et al., *Sex. Plant Reprod.,* 6:217-224 (1993)).

Signal Sequences for Targeting Proteins to Subcellular Compartments

Transport of a protein produced by transgenes to a subcellular compartment, such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized.

The presence of a signal sequence directs a polypeptide to either an intracellular organelle or subcellular compartment or for secretion to the apoplast. Many signal sequences are known in the art. See, for example, Becker et al., *Plant Mol. Biol.,* 20:49 (1992); Knox, C. et al., *Plant Mol. Biol.,* 9:3-17 (1987); Lerner et al., *Plant Physiol.,* 91:124-129 (1989); Frontes et al., *Plant Cell,* 3:483-496 (1991); Matsuoka et al., *Proc. Natl. Acad. Sci.,* 88:834 (1991); Gould et al., *J. Cell. Biol.,* 108:1657 (1989); Creissen et al., *Plant J.,* 2:129 (1991); Kalderon et al., *Cell,* 39:499-509 (1984); Steifel et al., *Plant Cell,* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein can then be extracted from a tissue of interest or from total biomass. Protein extraction from plant biomass can be accomplished by known methods which are discussed, for example, by Heney and Orr, *Anal. Biochem.,* 114:92-6 (1981).

According to a preferred embodiment, the transgenic plant provided for commercial production of foreign protein is a soybean plant. In another preferred embodiment, the biomass of interest is seed. For the relatively small number of transgenic plants that show higher levels of expression, a genetic map can be generated, primarily via conventional RFLP, PCR, and SSR analysis, which identifies the approximate chromosomal location of the integrated DNA molecule. For exemplary methodologies in this regard, see, Glick and Thompson, *Methods in Plant Molecular Biology and Biotechnology,* CRC Press, Inc., Boca Raton, 269:284 (1993). Map information concerning chromosomal location is useful for proprietary protection of a subject transgenic plant.

Wang et al. discuss "Large Scale Identification, Mapping and Genotyping of Single-Nucleotide Polymorphisms in the Human Genome," *Science,* 280:1077-1082 (1998), and similar capabilities are becoming increasingly available for the soybean genome. Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons would involve hybridizations, RFLP, PCR, SSR, and sequencing, all of which are conventional techniques. SNPs may also be used alone or in combination with other techniques.

Likewise, by means of the present invention, plants can be genetically engineered to express various phenotypes of agronomic interest. Through the transformation of soybean, the expression of genes can be altered to enhance disease resistance, insect resistance, herbicide resistance, agronomic, grain quality, and other traits. Transformation can also be used to insert DNA sequences which control or help control male-sterility. DNA sequences native to soybean, as well as non-native DNA sequences, can be transformed into soybean and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing or gene suppression) is desirable for several aspects of genetic engineering in plants.

Many techniques for gene silencing are well known to one of skill in the art, including, but not limited to, knock-outs (such as by insertion of a transposable element such as mu (Vicki Chandler, The Maize Handbook, Ch. 118 (Springer-Verlag 1994)) or other genetic elements such as a FRT and Lox that are used for site specific integrations, antisense technology (see, e.g., Sheehy et al., *PNAS USA*, 85:8805-8809 (1988); and U.S. Pat. Nos. 5,107,065, 5,453,566, and 5,759,829); co-suppression (e.g., Taylor, *Plant Cell*, 9:1245 (1997); Jorgensen, *Trends Biotech.*, 8(12):340-344 (1990); Flavell, *PNAS USA*, 91:3490-3496 (1994); Finnegan et al., *Bio/Technology*, 12:883-888 (1994); Neuhuber et al., *Mol. Gen. Genet.*, 244:230-241 (1994)); RNA interference (Napoli et al., *Plant Cell*, 2:279-289 (1990); U.S. Pat. No. 5,034,323; Sharp, *Genes Dev.*, 13:139-141 (1999); Zamore et al., *Cell*, 101:25-33 (2000); Montgomery et al., *PNAS USA*, 95:15502-15507 (1998)), virus-induced gene silencing (Burton et al., *Plant Cell*, 12:691-705 (2000); Baulcombe, *Curr. Op. Plant Bio.*, 2:109-113 (1999)); target-RNA-specific ribozymes (Haseloff et al., *Nature*, 334: 585-591 (1988)); hairpin structures (Smith et al., *Nature*, 407:319-320 (2000); WO 99/53050; WO 98/53083); MicroRNA (Aukerman & Sakai, *Plant Cell*, 15:2730-2741 (2003)); ribozymes (Steinecke et al., *EMBO J.*, 11:1525 (1992); Perriman et al., *Antisense Res. Dev.*, 3:253 (1993)); oligonucleotide mediated targeted modification (e.g., WO 03/076574 and WO 99/25853); Zn-finger targeted molecules (e.g., WO 01/52620, WO 03/048345, and WO 00/42219); and other methods or combinations of the above methods known to those of skill in the art.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant cultivar can be transformed with one or more cloned resistance genes to engineer plants that are resistant to specific pathogen strains. See, for example, Jones et al., *Science*, 266:789 (1994) (cloning of the tomato Cf-9 gene for resistance to *Cladosporium flavum*); Martin et al., *Science*, 262:1432 (1993) (tomato Pto gene for resistance to *Pseudomonas syringae* pv. tomato encodes a protein kinase); Mindrinos et al., *Cell*, 78:1089 (1994) (*Arabidopsis* RSP2 gene for resistance to *Pseudomonas syringae*); McDowell & Woffenden, *Trends Biotechnol.*, 21(4):178-83 (2003); and Toyoda et al., *Transgenic Res.*, 11 (6):567-82 (2002).

B. A gene conferring resistance to a pest, such as soybean cyst nematode. See, e.g., PCT Application WO 96/30517 and PCT Application WO 93/19181.

C. A *Bacillus thuringiensis* protein, a derivative thereof or a synthetic polypeptide modelled thereon. See, for example, Geiser et al., *Gene*, 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995, and 31998.

D. A lectin. See, for example, Van Damme et al., *Plant Molec. Biol.*, 24:25 (1994), who disclose the nucleotide sequences of several *Clivia miniata* mannose-binding lectin genes.

E. A vitamin-binding protein such as avidin. See, PCT Application US 93/06487, which teaches the use of avidin and avidin homologues as larvicides against insect pests.

F. An enzyme inhibitor, for example, a protease or proteinase inhibitor or an amylase inhibitor. See, for example, Abe et al., *J. Biol. Chem.*, 262:16793 (1987) (nucleotide sequence of rice cysteine proteinase inhibitor); Huub et al., *Plant Molec. Biol.*, 21:985 (1993) (nucleotide sequence of cDNA encoding tobacco proteinase inhibitor I); Sumitani et al., *Biosci. Biotech. Biochem.*, 57:1243 (1993) (nucleotide sequence of *Streptomyces nitrosporeus* α-amylase inhibitor); and U.S. Pat. No. 5,494,813 (Hepher and Atkinson, issued Feb. 27, 1996).

G. An insect-specific hormone or pheromone, such as an ecdysteroid or juvenile hormone, a variant thereof, a mimetic based thereon, or an antagonist or agonist thereof. See, for example, the disclosure by Hammock et al., *Nature*, 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, *J. Biol. Chem.*, 269:9 (1994) (expression cloning yields DNA coding for insect diuretic hormone receptor); Pratt et al., *Biochem. Biophys. Res. Comm.*, 163:1243 (1989) (an allostatin is identified in *Diploptera puntata*); Chattopadhyay et al., *Critical Reviews in Microbiology*, 30(1):33-54 (2004); Zjawiony, *J Nat Prod*, 67(2):300-310 (2004); Carlini & Grossi-de-Sa, *Toxicon*, 40(11):1515-1539 (2002); Ussuf et al., *Curr Sci.*, 80(7):847-853 (2001); Vasconcelos & Oliveira, *Toxicon*, 44(4):385-403 (2004). See also, U.S. Pat. No. 5,266,317 to Tomalski et al., which discloses genes encoding insect-specific, paralytic neurotoxins.

I. An insect-specific venom produced in nature by a snake, a wasp, etc. For example, see, Pang et al., *Gene*, 116:165 (1992), for disclosure of heterologous expression in plants of a gene coding for a scorpion insectotoxic peptide.

J. An enzyme responsible for a hyperaccumulation of a monoterpene, a sesquiterpene, a steroid, hydroxamic acid, a phenylpropanoid derivative, or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See, PCT Application WO 93/02197 (Scott et al.), which discloses the nucleotide sequence of a callase gene. DNA molecules which contain chitinase-encoding sequences can be obtained, for example, from the ATCC under Accession Nos. 39637 and 67152. See also, Kramer et al., *Insect Biochem. Molec. Biol.,* 23:691 (1993), who teach the nucleotide sequence of a cDNA encoding tobacco hornworm chitinase, and Kawalleck et al., *Plant Molec. Biol.,* 21:673 (1993), who provide the nucleotide sequence of the parsley ubi4-2 polyubiquitin gene, U.S. Pat. Nos. 7,145,060, 7,087,810, and 6,563,020.

L. A molecule that stimulates signal transduction. For example, see the disclosure by Botella et al., *Plant Molec. Biol.,* 24:757 (1994), of nucleotide sequences for mung bean calmodulin cDNA clones, and Griess et al., *Plant Physiol.,* 104:1467 (1994), who provide the nucleotide sequence of a maize calmodulin cDNA clone.

M. A hydrophobic moment peptide. See, PCT Application WO 95/16776 and U.S. Pat. No. 5,580,852, which disclose peptide derivatives of tachyplesin which inhibit fungal plant pathogens, and PCT Application WO 95/18855 and U.S. Pat. No. 5,607,914 which teaches synthetic antimicrobial peptides that confer disease resistance.

N. A membrane permease, a channel former or a channel blocker. For example, see the disclosure of Jaynes et al., *Plant Sci,* 89:43 (1993), of heterologous expression of a cecropin-β lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy et al., *Ann. Rev. Phytopathol.,* 28:451 (1990). Coat protein-mediated resistance has been conferred upon transformed plants against alfalfa mosaic virus, cucumber mosaic virus, and tobacco mosaic virus.

P. An insect-specific antibody or an immunotoxin derived therefrom. Thus, an antibody targeted to a critical metabolic function in the insect gut would inactivate an affected enzyme, killing the insect. See, Taylor et al., Abstract #497, Seventh Int'l Symposium on Molecular Plant-Microbe Interactions (Edinburgh, Scotland 1994) (enzymatic inactivation in transgenic tobacco via production of single-chain antibody fragments).

Q. A virus-specific antibody. See, for example, Tavladoraki et al., *Nature,* 366:469 (1993), who show that transgenic plants expressing recombinant antibody genes are protected from virus attack.

R. A developmental-arrestive protein produced in nature by a pathogen or a parasite. Thus, fungal endo-α-1, 4-D-polygalacturonases facilitate fungal colonization and plant nutrient release by solubilizing plant cell wall homo-α-1,4-D-galacturonase. See, Lamb et al., *Bio/Technology,* 10:1436 (1992). The cloning and characterization of a gene which encodes a bean endopolygalacturonase-inhibiting protein is described by Toubart et al., *Plant J.,* 2:367 (1992).

S. A developmental-arrestive protein produced in nature by a plant. For example, Logemann et al., *Bio/Technology,* 10:305 (1992), have shown that transgenic plants expressing the barley ribosome-inactivating gene have an increased resistance to fungal disease.

T. Genes involved in the Systemic Acquired Resistance (SAR) Response and/or the pathogenesis-related genes. Briggs, S., *Current Biology,* 5(2) (1995); Pieterse & Van Loon, *Curr. Opin. Plant Bio.,* 7(4):456-64 (2004); and Somssich, *Cell,* 113(7):815-6 (2003).

U. Antifungal genes. See, Cornelissen and Melchers, *Plant Physiol.,* 101:709-712 (1993); Parijs et al., *Planta,* 183:258-264 (1991); and Bushnell et al., *Can. J. of Plant Path.,* 20(2):137-149 (1998). See also, U.S. Pat. No. 6,875,907.

V. Detoxification genes, such as for fumonisin, beauvericin, moniliformin, and zearalenone and their structurally-related derivatives. See, for example, U.S. Pat. No. 5,792,931.

W. Cystatin and cysteine proteinase inhibitors. See, U.S. Pat. No. 7,205,453.

X. Defensin genes. See, WO 03/000863 and U.S. Pat. No. 6,911,577.

Y. Genes conferring resistance to nematodes, and in particular soybean cyst nematodes. See, e.g., PCT Applications WO 96/30517, WO 93/19181, and WO 03/033651; Urwin et al., *Planta,* 204:472-479 (1998); Williamson, *Curr Opin Plant Bio.,* 2(4):327-31 (1999).

Z. Genes that confer resistance to *Phytophthora* Root Rot, such as the Rps1, Rps1a, Rps1b, Rps1c, Rps1d, Rps1e, Rps1k, Rps2, Rps3a, Rps3b, Rps3c, Rps4, Rps5, Rps6, Rps7, and other Rps genes. See, for example, Shoemaker et al., *Phytophthora* Root Rot Resistance Gene Mapping in Soybean, Plant Genome IV Conference, San Diego, Calif. (1995).

AA. Genes that confer resistance to Brown Stem Rot, such as described in U.S. Pat. No. 5,689,035 and incorporated by reference for this purpose.

Any of the above-listed disease or pest resistance genes (A-AA) can be introduced into the claimed soybean cultivar through a cultivar of means including, but not limited to, transformation and crossing.

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee et al., *EMBO J.,* 7:1241 (1988) and Miki et al., *Theor. Appl. Genet.,* 80:449 (1990), respectively.

B. Glyphosate (resistance conferred by mutant 5-enolpyruvlshikimate-3-phosphate synthase (EPSPS) and aroA genes, respectively) and other phosphono compounds, such as glufosinate (phosphinothricin acetyl transferase (PAT) and *Streptomyces hygroscopicus* PAT bar genes), pyridinoxy or phenoxy propionic acids, and cyclohexanediones (ACCase inhibitor-encoding genes). See, for example, U.S. Pat. No. 4,940,835 to Shah et al., which discloses the nucleotide sequence of a form of EPSPS which can confer glyphosate resistance. U.S. Pat. No. 5,627,061 to Barry et al., also describes genes encoding EPSPS enzymes. See also, U.S. Pat. Nos. 6,566,587, 6,338,961, 6,248,876, 6,040,497, 5,804,425, 5,633,435, 5,145,783, 4,971,908, 5,312,910, 5,188,642, 4,940,835, 5,866,775, 6,225,114, 6,130,366, 5,310,667, 4,535,060, 4,769,061, 5,633,448, 5,510,471, RE 36,449, RE 37,287, and 5,491,288; and International Publications EP1173580, WO 01/66704, EP1173581, and EP1173582, which are incorporated herein by reference for this purpose. Glyphosate resistance is also imparted to plants that express a gene that encodes a glyphosate oxido-reductase enzyme, as described more fully in U.S. Pat. Nos. 5,776,760 and 5,463,175, which are incorporated herein by reference for this purpose. In addition, glyphosate resistance can be imparted to plants by the over expression of genes encoding glyphosate N-acetyltransferase. See, for example, U.S. Pat. No. 7,462,481. A DNA molecule encoding a mutant aroA gene can be obtained under ATCC Accession No. 39256, and the nucleotide sequence of the mutant gene is disclosed in U.S. Pat. No. 4,769,061 to Comai. European Patent Appl. No. 0 333 033 to Kumada et al. and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European Patent Appl. No. 0 242 246 to Leemans et al. DeGreef et al., *Bio/Technology*, 7:61 (1989) describe the production of transgenic plants that express chimeric bar genes coding for phosphinothricin acetyl transferase activity. Exemplary of genes conferring resistance to phenoxy propionic acids and cyclohexanediones, such as sethoxydim and haloxyfop are the Acc1-S1, Acc1-S2, and Acc2-S3 genes described by Marshall et al., *Theor. Appl. Genet.*, 83:435 (1992).

C. An herbicide that inhibits photosynthesis, such as a triazine (psbA and gs+ genes) and a benzonitrile (nitrilase gene). Przibila et al., *Plant Cell*, 3:169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441, and 67442. Cloning and expression of DNA coding for a glutathione S-transferase is described by Hayes et al., *Biochem. J.*, 285:173 (1992).

D. Acetohydroxy acid synthase, which has been found to make plants that express this enzyme resistant to multiple types of herbicides, has been introduced into a variety of plants. See, Hattori et al., *Mol. Gen. Genet.*, 246:419 (1995). Other genes that confer tolerance to herbicides include a gene encoding a chimeric protein of rat cytochrome P4507A1 and yeast NADPH-cytochrome P450 oxidoreductase (Shiota et al., *Plant Physiol.*, 106:17 (1994)); genes for glutathione reductase and superoxide dismutase (Aono et al., *Plant Cell Physiol.*, 36:1687 (1995)); and genes for various phosphotransferases (Datta et al., *Plant Mol. Biol.*, 20:619 (1992)).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306, 6,282, 837, 5,767,373, and International Publication WO 01/12825.

Any of the above listed herbicide genes (A-E) can be introduced into the claimed soybean cultivar through a variety of means including but not limited to transformation and crossing.

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See, Knultzon et al., *Proc. Natl. Acad. Sci. USA*, 89:2625 (1992).

B. Decreased phytate content: 1) Introduction of a phytase-encoding gene enhances breakdown of phytate, adding more free phosphate to the transformed plant. For example, see, Van Hartingsveldt et al., *Gene*, 127:87 (1993), for a disclosure of the nucleotide sequence of an *Aspergillus niger* phytase gene. 2) Up-regulation of a gene that reduces phytate content. In maize, this, for example, could be accomplished by cloning and then re-introducing DNA associated with one or more of the alleles, such as the LPA alleles, identified in maize mutants characterized by low levels of phytic acid, such as in Raboy et al., *Maydica*, 35:383 (1990), and/or by altering inositol kinase activity as in WO 02/059324, U.S. Publ. No. 2003/000901, WO 03/027243, U.S. Publ. No. 2003/0079247, WO 99/05298, U.S. Pat. Nos. 6,197,561, 6,291,224, 6,391,348, WO 2002/059324, U.S. Publ. No. 2003/0079247, WO 98/45448, WO 99/55882, and WO 01/04147.

C. Modified carbohydrate composition effected, for example, by transforming plants with a gene coding for an enzyme that alters the branching pattern of starch, or a gene altering thioredoxin, such as NTR and/or TRX (see, U.S. Pat. No. 6,531,648, which is incorporated by reference for this purpose), and/or a gamma zein knock out or mutant, such as cs27 or TUSC27 or en27 (see, U.S. Pat. Nos. 6,858,778 and 7,741,533 and U.S. Publ. No. 2005/0160488, which are incorporated by reference for this purpose). See, Shiroza et al., *J. Bacteriol.*, 170:810 (1988) (nucleotide sequence of *Streptococcus mutans* fructosyltransferase gene); Steinmetz et al., *Mol. Gen. Genet.*, 200:220 (1985) (nucleotide sequence of *Bacillus subtilis* levansucrase gene); Pen et al., *Bio/Technology*, 10:292 (1992) (production of transgenic plants that express *Bacillus licheniformis* alpha-amylase); Elliot et al., *Plant Molec. Biol.*, 21:515 (1993) (nucleotide sequences of tomato invertase genes); Sogaard et al., *J. Biol. Chem.*, 268:22480 (1993) (site-directed mutagenesis of barley alpha-amylase gene); Fisher et al., *Plant Physiol.*, 102:1045 (1993) (maize endosperm starch branching enzyme II); WO 99/10498 (improved digestibility and/or starch extraction through modification of UDP-D-xylose 4-epimerase, Fragile 1 and 2, Ref 1, HCHL, C4H); U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

D. Elevated oleic acid via FAD-2 gene modification and/or decreased linolenic acid via FAD-3 gene modification. See, U.S. Pat. Nos. 6,063,947, 6,323,392, and International Publication WO 93/11245. Linolenic acid is one of the five most abundant fatty acids in soybean seeds. The low oxidative stability of linolenic acid is one reason that soybean oil undergoes partial hydrogenation. When partially hydrogenated, all unsaturated fatty acids form trans fats. Soybeans are the largest source of edible-oils in the U.S. and 40% of soybean oil production is partially hydrogenated. The consumption of trans fats increases the risk of heart disease. Regulations banning trans fats have encouraged the development of low linolenic soybeans. Soybeans containing low linolenic acid percentages create a more stable oil requiring hydrogenation less often. This provides trans-fat free alternatives in products such as cooking oil.

E. Altering conjugated linolenic or linoleic acid content, such as in WO 01/12800. Altering LEC1, AGP, Dek1, Superal1, mi1ps, and various Ipa genes, such as Ipa1, Ipa3, hpt, or hggt. See, for example, WO 02/42424, WO 98/22604, WO 03/011015, WO 02/057439, WO 03/011015, U.S. Pat. Nos. 6,423,886, 6,197,561, 6,825,397, 7,157,621, U.S. Publ. No. 2003/0079247, and Rivera-Madrid, R. et al., *Proc. Natl. Acad. Sci.*, 92:5620-5624 (1995).

F. Altered antioxidant content or composition, such as alteration of tocopherol or tocotrienols. See, for example, U.S. Pat. Nos. 6,787,683, 7,154,029, WO 00/68393 (involving the manipulation of antioxidant levels through alteration of a phytl prenyl transferase (ppt)); WO 03/082899 (through alteration of a homogentisate geranyl geranyl transferase (hggt)).

G. Altered essential seed amino acids. See, for example, U.S. Pat. No. 6,127,600 (method of increasing accumulation of essential amino acids in seeds); U.S. Pat. No. 6,080,913 (binary methods of increasing accumulation of essential amino acids in seeds); U.S. Pat. No. 5,990,389 (high lysine); U.S. Pat. No. 5,850,016 (alteration of amino acid compositions in seeds); U.S. Pat. No. 5,885,802 (high methionine); U.S. Pat. No. 5,885,801 (high threonine); U.S. Pat. No. 6,664,445 (plant amino acid biosynthetic enzymes); U.S. Pat. No. 6,459,019 (increased lysine and threonine); U.S. Pat. No. 6,441,274 (plant tryptophan synthase beta subunit); U.S. Pat. No. 6,346,403 (methionine metabolic enzymes); U.S. Pat. No. 5,939,599 (high sulfur); U.S. Pat. No. 5,912,414 (increased methionine); U.S. Pat. No. 5,633,436 (increasing sulfur amino acid content); U.S. Pat. No. 5,559,223 (synthetic storage proteins with defined structure containing programmable levels of essential amino acids for improvement of the nutritional value of plants); U.S. Pat. No. 6,194,638 (hemicellulose); U.S. Pat. No. 7,098,381 (UDPGdH); U.S. Pat. No. 6,194,638 (RGP); U.S. Pat. Nos. 6,399,859, 6,930,225, 7,179,955, and 6,803,498; U.S. Publ. No. 2004/0068767; WO 99/40209 (alteration of amino acid compositions in seeds); WO 99/29882 (methods for altering amino acid content of proteins); WO 98/20133 (proteins with enhanced levels of essential amino acids); WO 98/56935 (plant amino acid biosynthetic enzymes); WO 98/45458 (engineered seed protein having higher percentage of essential amino acids); WO 98/42831 (increased lysine); WO 96/01905 (increased threonine); WO 95/15392 (increased lysine); WO 01/79516; and WO 00/09706 (Ces A: cellulose synthase).

4. Genes that Control Male Sterility:

There are several methods of conferring genetic male sterility available, such as multiple mutant genes at separate locations within the genome that confer male sterility, as disclosed in U.S. Pat. Nos. 4,654,465 and 4,727,219 to Brar et al., and chromosomal translocations as described by Patterson in U.S. Pat. Nos. 3,861,709 and 3,710,511. In addition to these methods, Albertsen et al., U.S. Pat. No. 5,432,068, describes a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on," the promoter, which in turn allows the gene that confers male fertility to be transcribed.

A. Introduction of a deacetylase gene under the control of a tapetum-specific promoter and with the application of the chemical N-Ac-PPT. See, International Publication WO 01/29237.

B. Introduction of various stamen-specific promoters. See, International Publications WO 92/13956 and WO 92/13957.

C. Introduction of the barnase and the barstar genes. See, Paul et al., *Plant Mol. Biol.*, 19:611-622 (1992).

For additional examples of nuclear male and female sterility systems and genes, see also, U.S. Pat. Nos. 5,859,341, 6,297,426, 5,478,369, 5,824,524, 5,850,014, and 6,265,640, all of which are hereby incorporated by reference.

5. Genes that Create a Site for Site Specific DNA Integration:

This includes the introduction of FRT sites that may be used in the FLP/FRT system and/or Lox sites that may be used in the Cre/loxP system. See, for example, Lyznik et al., Site-Specific Recombination for Genetic Engineering in Plants, *Plant Cell Rep*, 21:925-932 (2003) and WO 99/25821, which are hereby incorporated by reference. Other systems that may be used include the Gin recombinase of phage Mu (Maeser et al. (1991); Vicki Chandler, The Maize Handbook, Ch. 118 (Springer-Verlag 1994)); the Pin recombinase of *E. coli* (Enomoto et al. (1983)); and the R/RS system of the pSR1 plasmid (Araki et al. (1992)).

6. Genes that Affect Abiotic Stress Resistance:

Genes that affect abiotic stress resistance (including but not limited to flowering, pod and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; U.S. Publ. No. 2004/0148654 and WO 01/36596, where abscisic acid is altered in plants resulting in improved plant phenotype, such as increased yield and/or increased tolerance to abiotic stress; WO 2000/006341, WO 04/090143, U.S. Pat. Nos. 7,531,723 and 6,992,237, where cytokinin expression is modified resulting in plants with increased stress tolerance, such as drought tolerance, and/or increased yield. See also, WO 02/02776, WO 2003/052063, JP 2002281975, U.S. Pat. No. 6,084,153, WO 01/64898, and U.S. Pat. Nos. 6,177,275 and 6,107,547 (enhancement of nitrogen utilization and altered nitrogen responsiveness). For ethylene alteration, see, U.S. Publ. Nos. 2004/0128719, 2003/0166197, and WO 2000/32761. For plant transcription factors or transcriptional regulators of abiotic stress, see, e.g., U.S. Publ. Nos. 2004/0098764 or 2004/0078852.

Other genes and transcription factors that affect plant growth and agronomic traits, such as yield, flowering, plant growth, and/or plant structure, can be introduced or introgressed into plants. See, e.g., WO 97/49811 (LHY), WO 98/56918 (ESD4), WO 97/10339, U.S. Pat. No. 6,573,430 (TFL), U.S. Pat. No. 6,713,663 (FT), U.S. Pat. Nos. 6,794,560, 6,307,126 (GAI), WO 96/14414 (CON), WO 96/38560, WO 01/21822 (VRN1), WO 00/44918 (VRN2), WO 99/49064 (GI), WO 00/46358 (FRI), WO 97/29123, WO 99/09174 (D8 and Rht), WO 2004/076638, and WO 004/031349 (transcription factors).

Methods for Soybean Transformation

Numerous methods for plant transformation have been developed including biological and physical plant transformation protocols. See, for example, Miki et al., "Procedures for Introducing Foreign DNA into Plants," in *Methods in Plant Molecular Biology and Biotechnology*, Glick and Thompson Eds., CRC Press, Inc., Boca Raton, pp. 67-88 (1993). In addition, expression vectors and in-vitro culture methods for plant cell or tissue transformation and regeneration of plants are available. See, for example, Gruber et al., "Vectors for Plant Transformation," in *Methods in Plant Molecular Biology and Biotechnology*, Glick and Thompson Eds., CRC Press, Inc., Boca Raton, pp. 89-119 (1993).

A. *Agrobacterium*-mediated Transformation—One method for introducing an expression vector into plants is based on the natural transformation system of *Agrobacterium*. See, for example, Horsch et al., *Science,* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes,* respectively, carry genes responsible for genetic transformation of the plant. See, for example, Kado, C. I., *Crit. Rev. Plant Sci.,* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports,* 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation where DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.,* 5:27 (1987); Sanford, J. C., *Trends Biotech.,* 6:299 (1988); Klein et al., *Bio/Tech.,* 6:559-563 (1988); Sanford, J. C., *Physiol Plant,* 7:206 (1990); Klein et al., *Biotechnology,* 10:268 (1992). See also, U.S. Pat. No. 5,015,580 (Christou et al.), issued May 14, 1991 and U.S. Pat. No. 5,322,783 (Tomes et al.), issued Jun. 21, 1994.

Another method for physical delivery of DNA to plants is sonication of target cells. Zhang et al., *Bio/Technology,* 9:996 (1991). Alternatively, liposome and spheroplast fusion have been used to introduce expression vectors into plants. Deshayes et al., *EMBO J.,* 4:2731 (1985); Christou et al., *Proc Natl. Acad. Sci. USA,* 84:3962 (1987). Direct uptake of DNA into protoplasts using $CaCl_2$ precipitation, polyvinyl alcohol or poly-L-ornithine have also been reported. Hain et al., *Mol. Gen. Genet.,* 199:161 (1985) and Draper et al., *Plant Cell Physiol.,* 23:451 (1982). Electroporation of protoplasts and whole cells and tissues have also been described (Donn et al., In Abstracts of VIIth International Congress on Plant Cell and Tissue Culture IAPTC, A2-38, p. 53 (1990); D'Halluin et al., *Plant Cell,* 4:1495-1505 (1992); and Spencer et al., *Plant Mol. Biol.,* 24:51-61 (1994)).

Following transformation of soybean target tissues, expression of the above-described selectable marker genes allows for preferential selection of transformed cells, tissues, and/or plants, using regeneration and selection methods well known in the art.

The foregoing methods for transformation would typically be used for producing a transgenic cultivar. The transgenic cultivar could then be crossed with another (non-transformed or transformed) cultivar in order to produce a new transgenic cultivar. Alternatively, a genetic trait that has been engineered into a particular soybean line using the foregoing transformation techniques could be moved into another line using traditional backcrossing techniques that are well known in the plant breeding arts. For example, a backcrossing approach could be used to move an engineered trait from a public, non-elite cultivar into an elite cultivar, or from a cultivar containing a foreign gene in its genome into a cultivar or cultivars that do not contain that gene. As used herein, "crossing" can refer to a simple x by y cross or the process of backcrossing depending on the context.

Genetic Marker Profile Through SSR and First Generation Progeny

In addition to phenotypic observations, a plant can also be identified by its genotype. The genotype of a plant can be characterized through a genetic marker profile which can identify plants of the same cultivar, or a related cultivar, or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) (which are also referred to as Microsatellites), and Single Nucleotide Polymorphisms (SNPs). For example, see, Cregan et al., "An Integrated Genetic Linkage Map of the Soybean Genome," *Crop Science,* 39:1464-1490 (1999) and Berry et al., "Assessing Probability of Ancestry Using Simple Sequence Repeat Profiles: Applications to Maize Inbred Lines and Soybean Varieties," *Genetics,* 165:331-342 (2003), each of which are incorporated by reference herein in their entirety.

Particular markers used for these purposes are not limited to any particular set of markers, but are envisioned to include any type of marker and marker profile which provides a means of distinguishing varieties. One method of comparison is to use only homozygous loci for soybean cultivar 91030603.

Primers and PCR protocols for assaying these and other markers are disclosed in the Soybase (sponsored by the USDA Agricultural Research Service and Iowa State University). In addition to being used for identification of soybean cultivar 91030603, and plant parts and plant cells of soybean cultivar 91030603, the genetic profile may be used to identify a soybean plant produced through the use of soybean cultivar 91030603 or to verify a pedigree for progeny plants produced through the use of soybean cultivar 91030603. The genetic marker profile is also useful in breeding and developing backcross conversions.

The present invention provides in one embodiment a soybean plant cultivar characterized by molecular and physiological data obtained from the representative sample of said cultivar deposited with the Provasoli-Guillard National Center for Marine Algae and Microbiota (NCMA). Further provided by the invention is a soybean plant formed by the combination of the disclosed soybean plant or plant cell with another soybean plant or cell and comprising the homozygous alleles of the cultivar.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by polymerase chain reaction (PCR), thereby eliminating the need for labor-intensive Southern hybridization. PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing varieties it is preferable if all SSR profiles are performed in the same lab.

Primers used are publicly available and may be found in the Soybase or Cregan supra. See also, PCT Publication No. WO 99/31964 (Nucleotide Polymorphisms in Soybean); U.S. Pat. No. 6,162,967 (Positional Cloning of Soybean Cyst Nematode Resistance Genes); and U.S. Pat. No. 7,288,386 (Soybean Sudden Death Syndrome Resistant Soybeans and Methods of Breeding and Identifying Resistant Plants), the disclosure of which are incorporated herein by reference.

The SSR profile of soybean plant 91030603 can be used to identify plants comprising soybean cultivar 91030603 as a parent, since such plants will comprise the same homozygous alleles as soybean cultivar 91030603. Because the soybean cultivar is essentially homozygous at all relevant loci, most loci should have only one type of allele present. In contrast, a genetic marker profile of an $F_1$ progeny should be the sum of those parents, e.g., if one parent was homozygous for allele x at a particular locus, and the other parent homozygous for allele y at that locus, then the $F_1$ progeny will be xy (heterozygous) at that locus. Subsequent generations of progeny produced by selection and breeding are expected to be of genotype x (homozygous), y (homozygous), or xy (heterozygous) for that locus position. When the $F_1$ plant is selfed or sibbed for successive filial generations, the locus should be either x or y for that position.

In addition, plants and plant parts substantially benefiting from the use of soybean cultivar 91030603 in their development, such as soybean cultivar 91030603 comprising a backcross conversion, transgene, or genetic sterility factor, may be identified by having a molecular marker profile with a high percent identity to soybean cultivar 91030603. Such a percent identity might be 95%, 96%, 97%, 98%, 99%, 99.5%, or 99.9% identical to soybean cultivar 91030603.

The SSR profile of soybean cultivar 91030603 can also be used to identify essentially derived varieties and other progeny varieties developed from the use of soybean cultivar 91030603, as well as cells and other plant parts thereof. Such plants may be developed using the markers identified in WO 00/31964, U.S. Pat. Nos. 6,162,967, and 7,288,386. Progeny plants and plant parts produced using soybean cultivar 91030603 may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% genetic contribution from soybean cultivar, as measured by either percent identity or percent similarity. Such progeny may be further characterized as being within a pedigree distance of soybean cultivar 91030603, such as within 1, 2, 3, 4, or 5 or less cross-pollinations to a soybean plant other than soybean cultivar 91030603 or a plant that has soybean cultivar 91030603 as a progenitor. Unique molecular profiles may be identified with other molecular tools such as SNPs and RFLPs.

While determining the SSR genetic marker profile of the plants described supra, several unique SSR profiles may also be identified which did not appear in either parent of such plant. Such unique SSR profiles may arise during the breeding process from recombination or mutation. A combination of several unique alleles provides a means of identifying a plant cultivar, an $F_1$ progeny produced from such cultivar, and progeny produced from such cultivar.

Single-Gene Conversions

When the term "soybean plant" is used in the context of the present invention, this also includes any single gene conversions of that cultivar. The term single gene converted plant as used herein refers to those soybean plants which are developed by a plant breeding technique called backcrossing wherein essentially all of the morphological and physiological characteristics of a cultivar are recovered in addition to the single gene transferred into the cultivar via the backcrossing technique. By "essentially all" as used herein in the context of morphological and physiological characteristics it is meant that the characteristics of a plant are recovered that are otherwise present when compared in the same environment, other than occasional variant traits that might arise during backcrossing or direct introduction of a transgene. It is understood that a locus introduced by backcrossing may or may not be transgenic in origin, and thus the term backcrossing specifically includes backcrossing to introduce loci that were created by genetic transformation.

Backcrossing methods can be used with the present invention to improve or introduce a characteristic into the cultivar. The term "backcrossing" as used herein refers to the repeated crossing of a hybrid progeny back to the recurrent parent, i.e., backcrossing 1, 2, 3, 4, 5, 6, 7, 8, or more times to the recurrent parent. The parental soybean plant that contributes the gene for the desired characteristic is termed the nonrecurrent or donor parent. This terminology refers to the fact that the nonrecurrent parent is used one time in the backcross protocol and therefore does not recur. The parental soybean plant to which the gene or genes from the nonrecurrent parent are transferred is known as the recurrent parent as it is used for several rounds in the backcrossing protocol (Poehlman & Sleper (1994); Fehr, Principles of Cultivar Development, pp. 261-286 (1987)). In a typical backcross protocol, the original cultivar of interest (recurrent parent) is crossed to a second cultivar (nonrecurrent parent) that carries the single gene of interest to be transferred. The resulting progeny from this cross are then crossed again to the recurrent parent and the process is repeated until a soybean plant is obtained wherein essentially all of the morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original cultivar. To accomplish this, a single gene of the recurrent cultivar is modified or substituted with the desired gene from the nonrecurrent parent, while retaining essentially all of the rest of the genetic, and therefore the morphological and physiological constitution of the original cultivar. The choice of the particular nonrecurrent parent will depend on the purpose of the backcross; one of the major purposes is to add some agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new cultivar but that can be improved by backcrossing techniques. Single gene traits may or may not be transgenic. Examples of these traits include, but are not limited to, male sterility, waxy starch, herbicide resistance, resistance for bacterial, fungal, or viral disease, insect resistance, male fertility, enhanced nutritional quality, industrial usage, yield stability, and yield enhancement. These genes are generally inherited through the nucleus. Several of these single gene traits are described in U.S. Pat. Nos. 5,959,185, 5,973,234, and 5,977,445, the disclosures of which are specifically hereby incorporated by reference.

Introduction of a New Trait or Locus into Soybean Cultivar 91030603

Cultivar 91030603 represents a new base genetic cultivar into which a new locus or trait may be introgressed. Direct transformation and backcrossing represent two important methods that can be used to accomplish such an introgression. The term backcross conversion and single locus conversion are used interchangeably to designate the product of a backcrossing program.

Backcross Conversions of Soybean Cultivar 91030603

A backcross conversion of soybean cultivar 91030603 occurs when DNA sequences are introduced through backcrossing (Hallauer et al., "Corn Breeding," *Corn and Corn Improvements*, No. 18, pp. 463-481 (1988)), with soybean cultivar 91030603 utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses, and the like. Molecular marker assisted breeding or selection may be utilized to reduce the number of backcrosses necessary to achieve the backcross conversion. For example, see, Openshaw, S. J. et al., Marker-assisted Selection in Backcross Breeding, *Proceedings Symposium of the Analysis of Molecular Data*, Crop Science Society of America, Corvallis, Oreg. (August 1994), where it is demonstrated that a backcross conversion can be made in as few as two backcrosses.

The complexity of the backcross conversion method depends on the type of trait being transferred (single genes or closely linked genes as compared to unlinked genes), the level of expression of the trait, the type of inheritance (cytoplasmic or nuclear), and the types of parents included in the cross. It is understood by those of ordinary skill in the art that for single gene traits that are relatively easy to classify, the backcross method is effective and relatively easy to manage. (See, Hallauer et al., *Corn and Corn Improvement*, Sprague and Dudley, Third Ed. (1998)). Desired traits that may be transferred through backcross conversion include, but are not limited to, sterility (nuclear and cytoplasmic), fertility restoration, nutritional enhancements, drought tolerance, nitrogen utilization, altered fatty acid profile, low phytate, industrial enhancements, disease resistance (bacterial, fungal, or viral), insect resistance, and herbicide resistance. In addition, an introgression site itself, such as an FRT site, Lox site, or other site specific integration site, may be inserted by backcrossing and utilized for direct insertion of one or more genes of interest into a specific plant cultivar. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. The backcross is a form of inbreeding, and the features of the recurrent parent are automatically recovered after successive backcrosses. Poehlman, *Breeding Field Crops*, p. 204 (1987). Poehlman suggests from one to four or more backcrosses, but as noted above, the number of backcrosses necessary can be reduced with the use of molecular markers. Other factors, such as a genetically similar donor parent, may also reduce the number of backcrosses necessary. As noted by Poehlman, backcrossing is easiest for simply inherited, dominant, and easily recognized traits.

One process for adding or modifying a trait or locus in soybean cultivar 91030603 comprises crossing soybean cultivar 91030603 plants grown from soybean cultivar 91030603 seed with plants of another soybean cultivar that comprise the desired trait or locus, selecting $F_1$ progeny plants that comprise the desired trait or locus to produce selected $F_1$ progeny plants, crossing the selected progeny plants with the soybean cultivar 91030603 plants to produce backcross progeny plants, selecting for backcross progeny plants that have the desired trait or locus and the morphological characteristics of soybean cultivar 91030603 to produce selected backcross progeny plants, and backcrossing to soybean cultivar 91030603 three or more times in succession to produce selected fourth or higher backcross progeny plants that comprise said trait or locus. The modified soybean cultivar 91030603 may be further characterized as having the morphological and physiological characteristics of soybean cultivar 91030603 listed in Table 1 as determined at the 5% significance level when grown in the same environmental conditions and/or may be characterized by percent similarity or identity to soybean cultivar 91030603 as determined by SSR markers. The above method may be utilized with fewer backcrosses in appropriate situations, such as when the donor parent is highly related or markers are used in the selection step. Desired traits that may be used include those nucleic acids known in the art, some of which are listed herein, that will affect traits through nucleic acid expression or inhibition. Desired loci include the introgression of FRT, Lox, and other sites for site specific integration, which may also affect a desired trait if a functional nucleic acid is inserted at the integration site.

In addition, the above process and other similar processes described herein may be used to produce first generation progeny soybean seed by adding a step at the end of the process that comprises crossing soybean cultivar 91030603 with the introgressed trait or locus with a different soybean plant and harvesting the resultant first generation progeny soybean seed.

Tissue Culture

Further reproduction of the cultivar can occur by tissue culture and regeneration. Tissue culture of various tissues of soybeans and regeneration of plants therefrom is well known and widely published. For example, reference may be had to Komatsuda, T. et al., *Crop Sci.*, 31:333-337 (1991); Stephens, P. A. et al., *Theor. Appl. Genet.*, 82:633-635 (1991); Komatsuda, T. et al., *Plant Cell, Tissue and Organ Culture*, 28:103-113 (1992); Dhir, S. et al., *Plant Cell Reports*, 11:285-289 (1992); Pandey, P. et al., *Japan J. Breed.*, 42:1-5 (1992); and Shetty, K. et al., *Plant Science*, 81:245-251 (1992); as well as U.S. Pat. No. 5,024,944, issued Jun. 18, 1991 to Collins et al. and U.S. Pat. No. 5,008,200, issued Apr. 16, 1991 to Ranch et al. Thus, another aspect of this invention is to provide cells which upon growth and differentiation produce soybean plants having the morphological and physiological characteristics of soybean cultivar 91030603.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, petioles, leaves, stems, roots, root tips, anthers, pistils, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

Using Soybean Cultivar 91030603 to Develop Other Soybean Varieties

Soybean varieties such as soybean cultivar 91030603 are typically developed for use in seed and grain production. However, soybean varieties such as soybean cultivar 91030603 also provide a source of breeding material that may be used to develop new soybean varieties. Plant breeding techniques known in the art and used in a soybean plant breeding program include, but are not limited to, recurrent selection, bulk selection, mass selection, backcrossing, pedigree breeding, open pollination breeding, restriction fragment length polymorphism enhanced selection, genetic marker enhanced selection, making double haploids, and transformation. Often combinations of these techniques are used. The development of soybean varieties in a plant breeding program requires, in general, the development and evaluation of homozygous varieties. There are many analytical methods available to evaluate a new cultivar. The oldest and most traditional method of analysis is the observation of phenotypic traits, but genotypic analysis may also be used.

Additional Breeding Methods

This invention is directed to methods for producing a soybean plant by crossing a first parent soybean plant with a second parent soybean plant wherein either the first or second parent soybean plant is cultivar 91030603. The other parent may be any other soybean plant, such as a soybean plant that is part of a synthetic or natural population. Any such methods using soybean cultivar 91030603 are part of this invention: selfing, sibbing, backcrosses, mass selection, pedigree breeding, bulk selection, hybrid production, crosses to populations, and the like. These methods are well known in the art and some of the more commonly used breeding methods are described below. Descriptions of breeding methods can be found in one of several reference books (e.g., Allard, Principles of Plant Breeding (1960); Simmonds, Principles of Crop Improvement (1979); Sneep et al. (1979); Fehr, "Breeding Methods for Cultivar Development," Chapter 7, Soybean Improvement, Production and Uses, 2nd ed., Wilcox editor (1987)).

The following describes breeding methods that may be used with soybean cultivar 91030603 in the development of further soybean plants. One such embodiment is a method for developing a cultivar 91030603 progeny soybean plant in a soybean plant breeding program comprising: obtaining the soybean plant, or a part thereof, of cultivar 91030603, utilizing said plant, or plant part, as a source of breeding material, and selecting a soybean cultivar 91030603 progeny plant with molecular markers in common with cultivar 91030603 and/or with morphological and/or physiological characteristics selected from the characteristics listed in Tables 1 or 2. Breeding steps that may be used in the soybean plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of soybean cultivar 91030603 progeny soybean plants, comprising crossing cultivar 91030603 with another soybean plant, thereby producing a population of soybean plants which, on average, derive 50% of their alleles from soybean cultivar 91030603. A plant of this population may be selected and repeatedly selfed or sibbed with a soybean cultivar resulting from these successive filial generations. One embodiment of this invention is the soybean cultivar produced by this method and that has obtained at least 50% of its alleles from soybean cultivar 91030603.

One of ordinary skill in the art of plant breeding would know how to evaluate the traits of two plant varieties to determine if there is no significant difference between the two traits expressed by those varieties. For example, see, Fehr and Walt, *Principles of Cultivar Development*, pp. 261-286 (1987). Thus the invention includes soybean cultivar 91030603 progeny soybean plants comprising a combination of at least two cultivar 91030603 traits selected from the group consisting of those listed in Tables 1 and 2 or the cultivar 91030603 combination of traits listed in the Summary of the Invention, so that said progeny soybean plant is not significantly different for said traits than soybean cultivar 91030603 as determined at the 5% significance level when grown in the same environmental conditions. Using techniques described herein, molecular markers may be used to identify said progeny plant as a soybean cultivar 91030603 progeny plant. Mean trait values may be used to determine whether trait differences are significant, and preferably the traits are measured on plants grown under the same environmental conditions. Once such a cultivar is developed, its value is substantial since it is important to advance the germplasm base as a whole in order to maintain or improve traits such as yield, disease resistance, pest resistance, and plant performance in extreme environmental conditions.

Progeny of soybean cultivar 91030603 may also be characterized through their filial relationship with soybean cultivar 91030603, as for example, being within a certain number of breeding crosses of soybean cultivar 91030603. A breeding cross is a cross made to introduce new genetics into the progeny, and is distinguished from a cross, such as a self or a sib cross, made to select among existing genetic alleles. The lower the number of breeding crosses in the pedigree, the closer the relationship between soybean cultivar 91030603 and its progeny. For example, progeny produced by the methods described herein may be within 1, 2, 3, 4, or 5 breeding crosses of soybean cultivar 91030603.

As used herein, the term "plant" includes plant cells, plant protoplasts, plant cell tissue cultures from which soybean plants can be regenerated, plant calli, plant clumps, and plant cells that are intact in plants or parts of plants, such as embryos, pollen, ovules, flowers, pods, leaves, roots, root tips, anthers, cotyledons, hypocotyls, meristematic cells, stems, pistils, petiole, and the like.

Pedigree Breeding

Pedigree breeding starts with the crossing of two genotypes, such as soybean cultivar 91030603 and another soybean cultivar having one or more desirable characteristics that is lacking or which complements soybean cultivar 91030603. If the two original parents do not provide all the desired characteristics, other sources can be included in the breeding population. In the pedigree method, superior plants are selfed and selected in successive filial generations. In the succeeding filial generations, the heterozygous condition gives way to homogeneous varieties as a result of self-pollination and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$; etc. After a sufficient amount of inbreeding, successive filial generations will serve to increase seed of the developed cultivar. Preferably, the developed cultivar comprises homozygous alleles at about 95% or more of its loci.

In addition to being used to create a backcross conversion, backcrossing can also be used in combination with pedigree breeding. As discussed previously, backcrossing can be used to transfer one or more specifically desirable traits from one cultivar, the donor parent, to a developed cultivar called the recurrent parent, which has overall good agronomic characteristics yet lacks that desirable trait or traits. However, the same procedure can be used to move the progeny toward the genotype of the recurrent parent, but at the same time retain many components of the nonrecurrent parent by stopping the backcrossing at an early stage and proceeding with selfing and selection. For example, a soybean cultivar may be crossed with another cultivar to produce a first generation progeny plant. The first generation progeny plant may then be backcrossed to one of its parent varieties to create a $BC_1$ or $BC_2$. Progeny are selfed and selected so that the newly developed cultivar has many of the attributes of the recurrent parent and yet several of the desired attributes of the nonrecurrent parent. This approach leverages the value and strengths of the recurrent parent for use in new soybean varieties.

Therefore, an embodiment of this invention is a method of making a backcross conversion of soybean cultivar 91030603, comprising the steps of crossing a plant of soybean cultivar 91030603 with a donor plant comprising a desired trait, selecting an $F_1$ progeny plant comprising the desired trait, and backcrossing the selected $F_1$ progeny plant to a plant of soybean cultivar 91030603. This method may further comprise the step of obtaining a molecular marker profile of soybean cultivar 91030603 and using the molecular marker profile to select for a progeny plant with the desired trait and the molecular marker profile of soybean cultivar 91030603. In one embodiment, the desired trait is a mutant gene or transgene present in the donor parent.

Recurrent Selection and Mass Selection

Recurrent selection is a method used in a plant breeding program to improve a population of plants. Soybean cultivar 91030603 is suitable for use in a recurrent selection program. The method entails individual plants cross pollinating with each other to form progeny. The progeny are grown and the superior progeny selected by any number of selection methods, which include individual plant, half-sib progeny, full-sib progeny, and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic cultivar. A synthetic cultivar is the resultant progeny formed by the intercrossing of several selected varieties.

Mass selection is a useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk, and then using a sample of the seed harvested in bulk to plant the next generation. Also, instead of self-pollination, directed pollination could be used as part of the breeding program.

Mutation Breeding

Mutation breeding is another method of introducing new traits into soybean cultivar 91030603. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil)), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in Fehr, "Principles of Cultivar Development," Macmillan Publishing Company (1993). In addition, mutations created in other soybean plants may be used to produce a backcross conversion of soybean cultivar 91030603 that comprises such mutation.

Breeding with Molecular Markers

Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs), may be used in plant breeding methods utilizing soybean cultivar 91030603.

Isozyme Electrophoresis and RFLPs have been widely used to determine genetic composition. Shoemaker and Olsen, Molecular Linkage Map of Soybean (*Glycine max* L. Merr.), pp. 6.131-6.138 (1993). In S. J. O'Brien (ed.), *Genetic Maps: Locus Maps of Complex Genomes*, Cold Spring Harbor Laboratory Press, Cold Spring Harbor, N.Y., developed a molecular genetic linkage map that consisted of 25 linkage groups with about 365 RFLP, 11 RAPD, 3 classical markers, and 4 isozyme loci. See also, Shoemaker, R. C., 1994 RFLP Map of Soybean, pp. 299-309; In R. L. Phillips and I. K. Vasil (ed.), *DNA-based markers in plants*, Kluwer Academic Press Dordrecht, the Netherlands.

SSR technology is currently the most efficient and practical marker technology. More marker loci can be routinely used, and more alleles per marker locus can be found, using SSRs in comparison to RFLPs. For example, Diwan and Cregan described a highly polymorphic microsatellite loci in soybean with as many as 26 alleles. (Diwan, N. and Cregan. P. B., Automated sizing of fluorescent-labelled simple sequence repeat (SSR) markers to assay genetic variation in Soybean, *Theor. Appl. Genet.*, 95:220-225 (1997). Single Nucleotide Polymorphisms may also be used to identify the unique genetic composition of the invention and progeny varieties retaining that unique genetic composition. Various molecular marker techniques may be used in combination to enhance overall resolution.

Soybean DNA molecular marker linkage maps have been rapidly constructed and widely implemented in genetic studies. One such study is described in Cregan et al., "An Integrated Genetic Linkage Map of the Soybean Genome," *Crop Science*, 39:1464-1490 (1999). Sequences and PCR conditions of SSR Loci in Soybean, as well as the most current genetic map, may be found in Soybase on the World Wide Web.

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Production of Double Haploids

The production of double haploids can also be used for the development of plants with a homozygous phenotype in the breeding program. For example, a soybean plant for which soybean cultivar 91030603 is a parent can be used to produce double haploid plants. Double haploids are produced by the doubling of a set of chromosomes (1 N) from a heterozygous plant to produce a completely homozygous individual. For example, see, Wan et al., "Efficient Production of Doubled Haploid Plants Through Colchicine Treatment of Anther-Derived Maize Callus," *Theoretical and Applied Genetics*, 77:889-892 (1989) and U.S. Pat. No. 7,135,615. This can be advantageous because the process omits the generations of selfing needed to obtain a homozygous plant from a heterozygous source.

Haploid induction systems have been developed for various plants to produce haploid tissues, plants and seeds. The haploid induction system can produce haploid plants from any genotype by crossing a selected line (as female) with an inducer line. Such inducer lines for maize include Stock 6 (Coe, *Am. Nat.*, 93:381-382 (1959); Sharkar and Coe, *Genetics*, 54:453-464 (1966); KEMS (Deimling, Roeber, and Geiger, *Vortr. Pflanzenzuchtg*, 38:203-224 (1997); or KMS and ZMS (Chalyk, Bylich & Chebotar, *MNL*, 68:47 (1994); Chalyk & Chebotar, *Plant Breeding*, 119:363-364 (2000)); and indeterminate gametophyte (ig) mutation (Kermicle, *Science*, 166:1422-1424 (1969). The disclosures of which are incorporated herein by reference.

Methods for obtaining haploid plants are also disclosed in Kobayashi, M. et al., *Journ. of Heredity*, 71(1):9-14 (1980); Pollacsek, M., Agronomie (Paris) 12(3):247-251 (1992); Cho-Un-Haing et al., *Journ. of Plant Biol.*, 39(3):185-188 (1996); Verdoodt, L. et al., 96(2):294-300 (February 1998); Genetic Manipulation in Plant Breeding, Proceedings International Symposium Organized by EUCARPIA, Berlin, Germany (Sep. 8-13, 1985); Chalyk et al., *Maize Genet Coop.*, Newsletter 68:47 (1994).

Thus, an embodiment of this invention is a process for making a substantially homozygous soybean cultivar 91030603 progeny plant by producing or obtaining a seed from the cross of soybean cultivar 91030603 and another soybean plant and applying double haploid methods to the $F_1$ seed or $F_1$ plant or to any successive filial generation. Based on studies in maize and currently being conducted in soybean, such methods would decrease the number of generations required to produce a cultivar with similar genes or characteristics to soybean cultivar 91030603. See, Bernardo, R. and Kahler, A. L., *Theor. Appl. Genet.*, 102:986-992 (2001).

In particular, a process of making seed retaining the molecular marker profile of soybean cultivar 91030603 is contemplated, such process comprising obtaining or producing $F_1$ seed for which soybean cultivar 91030603 is a parent, inducing doubled haploids to create progeny without the occurrence of meiotic segregation, obtaining the molecular marker profile of soybean cultivar 91030603, and selecting progeny that retain the molecular marker profile of soybean cultivar 91030603.

Descriptions of other breeding methods that are commonly used for different traits and crops can be found in one of several reference books (e.g., Allard (1960); Simmonds (1979); Sneep et al. (1979); Fehr (1987)).

INDUSTRIAL USES

The seed of soybean cultivar 91030603, the plant produced from the seed, the hybrid soybean plant produced from the crossing of the cultivar with any other soybean plant, hybrid seed, and various parts of the hybrid soybean plant can be utilized for human food, livestock feed, and as a raw material in industry. The soybean seeds produced by soybean cultivar 91030603 can be crushed, or a component of the soybean seeds can be extracted, in order to comprise a commodity plant product, such as protein concentrate, protein isolate, soybean hulls, meal, flour, or oil for a food or feed product.

Soybean cultivar 91030603 can be used to produce soybean oil. To produce soybean oil, the soybeans harvested from soybean cultivar 91030603 are cracked, adjusted for moisture content, rolled into flakes and the oil is solvent-extracted from the flakes with commercial hexane. The oil is then refined, blended for different applications, and sometimes hydrogenated. Soybean oils, both liquid and partially hydrogenated, are used domestically and exported, sold as "vegetable oil" or are used in a wide variety of processed foods.

Soybean cultivar 91030603 can be used to produce meal. After oil is extracted from whole soybeans harvested from soybean cultivar 91030603, the remaining material or "meal" is "toasted" (a misnomer because the heat treatment is with moist steam) and ground in a hammer mill. Soybean meal is an essential element of the American production method of growing farm animals, such as poultry and swine, on an industrial scale that began in the 1930s; and more recently the aquaculture of catfish. Ninety-eight percent of the U.S. soybean crop is used for livestock feed. Soybean meal is also used in lower end dog foods. Soybean meal produced from soybean cultivar 91030603 can also be used to produce soybean protein concentrate and soybean protein isolate.

In addition to soybean meal, soybean cultivar 91030603 can be used to produce soy flour. Soy flour refers to defatted soybeans where special care was taken during desolventizing (not toasted) to minimize denaturation of the protein and to retain a high Nitrogen Solubility Index (NSI) in making the flour. Soy flour is the starting material for production of soy concentrate and soy protein isolate. Defatted soy flour is obtained from solvent extracted flakes, and contains less than 1% oil. Full-fat soy flour is made from unextracted, dehulled beans, and contains about 18% to 20% oil. Due to its high oil content, a specialized Alpine Fine Impact Mill must be used for grinding rather than the more common hammer mill. Low-fat soy flour is made by adding back some oil to defatted soy flour. The lipid content varies according to specifications, usually between 4.5% and 9%. High-fat soy flour can also be produced by adding back soybean oil to defatted flour at the level of 15%. Lecithinated soy flour is made by adding soybean lecithin to defatted, low-fat or high-fat soy flours to increase their dispersibility and impart emulsifying properties. The lecithin content varies up to 15%.

For human consumption, soybean cultivar 91030603 can be used to produce edible protein ingredients which offer a healthier, less expensive replacement for animal protein in meats, as well as in dairy-type products. The soybeans produced by soybean cultivar 91030603 can be processed to produce a texture and appearance similar to many other foods. For example, soybeans are the primary ingredient in many dairy product substitutes (e.g., soy milk, margarine, soy ice cream, soy yogurt, soy cheese, and soy cream cheese) and meat substitutes (e.g., veggie burgers). These substitutes are readily available in most supermarkets. Although soy milk does not naturally contain significant amounts of digestible calcium (the high calcium content of soybeans is bound to the insoluble constituents and remains in the soy pulp), many manufacturers of soy milk sell calcium-enriched products as well. Soy is also used in tempeh: the beans (sometimes mixed with grain) are fermented into a solid cake.

Additionally, soybean cultivar 91030603 can be used to produce various types of "fillers" in meat and poultry products. Food service, retail, and institutional (primarily school lunch and correctional) facilities regularly use such "extended" products, that is, products which contain soy fillers. Extension may result in diminished flavor, but fat and cholesterol are reduced by adding soy fillers to certain products. Vitamin and mineral fortification can be used to make soy products nutritionally equivalent to animal protein; the protein quality is already roughly equivalent.

Table 2 compares performance characteristics of soybean cultivar 91030603 to selected varieties of commercial value. Shown are the comparison numbers, cultivar names, performance characteristics, t values, and critical t values at the 0.05% and 0.01% levels of significance, respectively.

TABLE 2

PAIRED COMPARISONS

| Comp # | Year | # of Loc. | # of Obs. | Genotype | Mean Yld | t Value | Critical t @ .05 | Critical t @ .01 |
|---|---|---|---|---|---|---|---|---|
| 1 | 2019 | 18 | 36 | 91030603 | 58.6 | 3.58** | 1.69 | 2.44 |
|   |      |    |    | CX3762N  | 54.7 |        |      |      |

*Significant at 0.05 level of probability
**Significant at 0.01 level of probability As shown in Table 2, soybean cultivar 91030603 yields better than one commercial variety with the increase over CX3762N being significant at the 0.01 level of probability.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

DEPOSIT INFORMATION

Applicant has made a deposit of at least 625 seeds of the claimed soybean cultivar 91030603 with the Provasoli-Guillard National Center for Marine Algae and Microbiota (NCMA), 60 Bigelow Drive, East Boothbay, Me., 04544 USA. The seeds are deposited under NCMA Accession No. 202101082. The date of the deposit is Jan. 14, 2021. The deposit has been accepted under the Budapest Treaty and will be maintained in the NCMA depository for a period of 30 years, or 5 years after the most recent request, or for the enforceable life of the patent, whichever is longer, and will be replaced if necessary during that period. Upon issuance, all restrictions on the availability to the public of the deposit will be irrevocably removed consistent with all of the requirements of the Budapest Treaty and 37 C.F.R. §§ 1.801-1.809. Applicant does not waive any infringement of rights granted under this patent or under the Plant Variety Protection Act (7 USC 2321 et seq.).

While a number of exemplary aspects and embodiments have been discussed above, those of skill in the art will recognize certain modifications, permutations, additions and sub combinations thereof. It is therefore intended that the following appended claims and claims hereafter introduced are interpreted to include all such modifications, permutations, additions, and sub-combinations as are within their true spirit and scope.

What is claimed:

1. A plant of soybean cultivar 91030603, representative seed of said soybean cultivar having been deposited under NCMA Accession No. 202101082.

2. A seed that produces the plant of claim 1.

3. A cell of the plant of claim 1.

4. A tissue culture of regenerable cells comprising the cell of claim 3.

5. A method of soybean breeding, said method comprising crossing the plant of claim 1 with itself or a second soybean plant to produce soybean seed.

6. The method of claim 5, further defined as comprising crossing a plant of soybean cultivar 91030603 with a second soybean plant of a different genotype to produce hybrid soybean seed.

7. An $F_1$ hybrid soybean seed produced by the method of claim 6.

8. A method of producing a plant comprising an added desired trait, said method comprising introducing a transgene conferring the desired trait into the plant of claim 1.

9. The method of claim 8, wherein the desired trait is selected from the group consisting of male sterility, herbicide tolerance, insect or pest resistance, disease resistance, modified fatty acid metabolism, and modified carbohydrate metabolism.

10. A plant produced by the method of claim 8 or a selfed progeny thereof, wherein said plant or the selfed progeny thereof comprises the transgene and otherwise comprises all of the morphological and physiological characteristics of soybean cultivar 91030603.

11. A method of introducing a single locus conversion into a soybean plant, said method comprising:
(a) crossing a plant of soybean cultivar 91030603 with a second plant comprising a desired single locus to produce $F_1$ progeny plants, representative seed of said soybean cultivar 91030603 having been deposited under NCMA Accession No. 202101082;
(b) selecting at least a first progeny plant from step (a) that comprises the single locus to produce a selected progeny plant;
(c) crossing the selected progeny plant from step (b) with a plant of soybean cultivar 91030603 to produce at least a first backcross progeny plant that comprises the single locus; and
(d) repeating steps (b) and (c) with the first backcross progeny plant produced from step (c) used in place of the first progeny plant of step (b) during said repeating, wherein steps (b) and (c) are repeated until at least a backcross progeny plant is produced comprising the single locus conversion.

12. The method of claim 11, wherein the single locus confers a trait selected from the group consisting of male sterility, herbicide tolerance, insect or pest resistance, disease resistance, modified fatty acid metabolism, abiotic stress resistance, and modified carbohydrate metabolism.

13. A soybean plant of soybean cultivar 91030603, further comprising a single locus conversion, wherein the plant comprises the single locus conversion and otherwise comprises all of the morphological and physiological characteristics of soybean cultivar 91030603, representative seed of soybean cultivar 91030603 having been deposited under NCMA Accession No. 202101082.

14. The method of claim 6, wherein the method further comprises:
(a) crossing a plant grown from said hybrid soybean seed with itself or a different soybean plant to produce a seed of a progeny plant of a subsequent generation.

15. The method of claim 14, wherein the method further comprises:
(b) growing a progeny plant of a subsequent generation from said seed of the progeny plant of the subsequent generation and crossing the progeny plant of the subsequent generation with itself or a second plant to produce a progeny plant of a further subsequent generation.

16. The method of claim 15, wherein the method further comprises:
(c) repeating steps (a) and (b) using said progeny plant of the further subsequent generation from step (b) in place of the plant grown from said hybrid soybean seed in step (a), wherein steps (a) and (b) are repeated with sufficient inbreeding to produce an inbred soybean plant derived from the soybean cultivar 91030603.

17. A method of introducing a mutation into the genome of soybean cultivar 91030603, said method comprising applying a mutagen to the plant of claim 1, or a part thereof, wherein said mutagen is selected from the group consisting of ethyl methanesulfonate, gamma-rays, and sodium azide, and wherein the resulting plant comprises a genome mutation.

18. A mutagenized soybean plant produced by the method of claim 17, wherein the mutagenized soybean plant comprises a mutation in the genome and otherwise comprises all of the morphological and physiological characteristics of soybean cultivar 91030603.

19. A method of producing a commodity plant product, said method comprising obtaining the plant of claim 1 or a part thereof and producing said commodity plant product therefrom.

20. The method of claim 19, wherein the commodity plant product is protein concentrate, protein isolate, soybean hulls, meal, flour, or oil.

\* \* \* \* \*